US005733839A

United States Patent [19]

Espinoza et al.

[11] Patent Number: 5,733,839

[45] Date of Patent: Mar. 31, 1998

[54] CATALYSTS

[75] Inventors: Rafael Luis Espinoza; Jacobus Lucas Visagie; Peter Jacobus Van Berge; Franciscus Hermanus Bolder, all of Sasolburg, South Africa

[73] Assignee: Sastech (Proprietary) Limited, Johannesburg, South Africa

[21] Appl. No.: 631,658

[22] Filed: Apr. 2, 1996

[30] Foreign Application Priority Data

Apr. 7, 1995 [ZA] South Africa .......................... 95/2903

[51] Int. Cl.[6] ..................... B01J 23/42; B01J 23/72; B01J 23/56

[52] U.S. Cl. ..................... 502/336; 502/327; 502/331; 502/332; 502/334; 502/338; 502/339; 502/346

[58] Field of Search ..................... 502/325, 326, 502/327, 330, 331, 332, 334, 336, 338, 339, 345, 346

[56] References Cited

U.S. PATENT DOCUMENTS

| | | | |
|---|---|---|---|
| 3,472,794 | 10/1969 | Carter | 252/459 |
| 3,591,649 | 7/1971 | Kroll et al. | 260/667 |
| 3,830,752 | 8/1974 | Mikelson | 252/435 |
| 3,962,138 | 6/1976 | Ray | 252/462 |
| 3,969,271 | 7/1976 | Lester | 252/430 |
| 4,407,733 | 10/1983 | Birenstock | 502/174 |
| 4,413,064 | 11/1983 | Beuther et al. | 518/715 |
| 4,567,160 | 1/1986 | Nay | 502/326 |
| 4,605,679 | 8/1986 | Kobylinski | 518/700 |
| 4,626,521 | 12/1986 | Murib | 502/328 |
| 4,640,908 | 2/1987 | Dupin | 502/243 |
| 4,717,702 | 1/1988 | Beuther | 502/303 |
| 4,794,095 | 12/1988 | Iglesia | 502/241 |
| 4,801,573 | 1/1989 | Eri | 502/302 |
| 4,880,763 | 11/1989 | Eri | 502/302 |
| 4,992,406 | 2/1991 | Maudlin | 502/304 |
| 5,102,851 | 4/1992 | Eri et al. | 502/302 |
| 5,258,348 | 11/1993 | Van Buren | 502/328 |

FOREIGN PATENT DOCUMENTS

| | | |
|---|---|---|
| 167215 | of 0000 | European Pat. Off. . |
| 0127220 | 12/1984 | European Pat. Off. . |
| 0266898 | 5/1988 | European Pat. Off. . |
| 0434284 | 6/1991 | European Pat. Off. . |
| 0535790 | 4/1993 | European Pat. Off. . |
| 932662 | of 0000 | South Africa . |
| 2258414 | of 0000 | United Kingdom . |
| 9206784 | of 0000 | WIPO . |

*Primary Examiner*—Walter D. Griffin
*Assistant Examiner*—Thuan D. Dang
*Attorney, Agent, or Firm*—Ladas & Parry

[57] ABSTRACT

To prepare a Fischer-Tropsch catalyst, a slurry comprising a particular alumina carrier, water and an active component selected from the group consisting in cobalt (Co), iron (Fe) and mixtures thereof, is subjected to a sub-atmospheric pressure environment. The alumina carrier is thereby impregnated by the active component. The impregnated carrier is dried under a sub-atmospheric pressure environment. The dried impregnated carrier is calcined, thereby to obtain the Fischer-Tropsch catalyst.

17 Claims, 4 Drawing Sheets

CATALYSTS

This invention relates to catalysts. It relates in particular to a process for preparing a Fischer-Tropsch catalyst, and to a Fischer-Tropsch catalyst prepared by the process.

SUMMARY OF THE INVENTION

According to the invention, there is provided a process for preparing a Fischer-Tropsch catalyst, which process comprises subjecting a slurry comprising a particulate alumina carrier, water and an active component selected from the group consisting in cobalt (Co), iron (Fe) and mixtures thereof, to a sub-atmospheric pressure environment, thereby to impregnate the alumina carrier with the active component;

drying the impregnated carrier under a sub-atmospheric pressure environment; and calcining the dried impregnated carrier, thereby to obtain the Fischer-Tropsch catalyst.

The sub-atmospheric pressure environment during the impregnation may be at a pressure less than 20 kPa(a), and preferably at a pressure less than 10 kPa(a). Likewise, the sub-atmospheric pressure environment during the drying may be at a pressure less than 20 kPa(a), and preferably at a pressure less than 10 kPa(a).

The drying temperature is limited by the lower limit of the decomposition temperature of the active component, which is typically a nitrate salt so that the drying temperature is typically 70° C.–90° C.

The sub-atmospheric pressure environments can thus be obtained by placing the slurry in a suitable enclosed vessel, and drawing the required sub-atmospheric pressure or vacuum on the vessel.

While the impregnation and drying in the sub-atmospheric pressure or vacuum environments or conditions can be effected in two separate or distinct steps, they can, if desired, be effected in a single step, so that the impregnation is effected while the drying takes place.

The drying in the sub-atmospheric pressure environment may be continued until the moisture content of the impregnated carrier is below 20% by mass. Thereafter, the impregnated carrier may be dried further under non-sub-atmospheric pressure conditions to remove more water, particularly water of crystallization. The further drying may be effected by passing a drying medium, eg air, in co-current or counter-current fashion over the impregnated carrier. The drying temperature may then be between 100° C. and 180° C. Thus, for example, the further drying may be effected by means of hot air used to fluidize and dry the particulate carrier, eg in a tubular reactor, in which case the air flow is co-current. Instead, however, the further drying may be effected in a counter-current air drier, which may be a catalyst spray drier.

The calcination of the dried impregnated carrier thus converts or decomposes the active component to its oxide form. Thus, for example, the active component can be used in the form of a salt, eg $Co(NO_3)_2$, with the salt then being decomposed to the oxide of the active component, eg $Co_3O_4$. The calcining is thus effected in a calciner. For example, the calciner can be mounted to the lower end of a spray drier used for further drying of the carrier as hereinbefore described, with the dried carrier then falling directly into the calciner.

If desired, the calcined catalyst may be re-slurried with water together with at least one of the following: the active component, another active component, or a dopant as hereinafter described, with the resultant impregnated carrier then again being subjected to drying and calcination, as hereinbefore-described.

The process may include forming the slurry. In particular, the active component may initially be in the form of a water soluble compound of the component, and may then be dissolved in at least some of the water, prior to forming the slurry with the alumina carrier, so that formation of the slurry will then involve intimate admixing of the alumina carrier and a solution of the active component compound. Supersaturation during impregnation, which results in active component precursor crystallization, should be avoided during impregnation/drying. The supersaturation aspect is addressed through the slurry impregnation, while the vacuum drying at ~75° C. of the aqueous solution addresses the precursor crystallization aspect. Thus, the purpose is to inhibit or prevent the diffusion of the catalyst precursor to the outer rim of the carrier body during drying (which would result in an egg-shell distribution) and which is enhanced by slow drying rates. Vacuum drying of an aqueous impregnation solution at ~75° C. overcomes this problem, thereby also eliminating the option of using more volatile solvents, eg acetone, alcohol, etc, the use of which is also complicated by aspects such as: poorer solubilities of nitrates, for example ~35% less $Co(NO_3)_2$ is soluble in acetone as compared to water at room temperature; and the presence of high quantities of crystal waters, eg $Co (NO_3)_2.6H_2O$.

While the alumina carrier will typically not be structurally promoted, it is, however, envisaged that it can contain a structural promoter such as magnesium (Mg) or cerium (Ce) if desired, eg if it is desired to enhance the attrition resistance of the resultant catalyst which is obtained from the process of the invention.

Irrespective of whether or not the alumina carrier is structurally promoted, the process of the invention may, however, be categorized thereby that no promoter to enhance the activity of the resultant catalyst or to modify its selectivity, such as potassium (K), chromium (Cr), magnesium (Mg), zirconium (Zr), ruthenium (Ru), thorium (Th), hafnium (Hf), cerium (Ce), rhenium (Re), uranium (U), vanadium (V), titanium (Ti), manganese (Mn), nickel (Ni), molybdenum (Mo), wolfram (W), lanthanum (La), palladium (Pd), uranium (U), praseodymium (Pr), neodymium (Nd) or other elements from groups IA or IIA of the periodic table of the elements, is added to the slurry or to the impregnated carrier. Thus, the resultant catalyst will then contain no such synthesis enhancing promoter(s). As a result, the calcination of the dried impregnated carrier may be effected at a relatively low temperature, eg at a temperature below 350° C., and even below 300° C.

When the catalyst is to be used in a slurry bed reactor, it may be washed with a suitable washing medium, eg water, after the calcination, to remove unwanted contaminants, such as cobalt, which may have formed on the external surface of the catalyst in the form of a shell of cobalt, ie without alumina being present in the shell. This washing is preferably effected with agitation, which may be achieved through boiling of the water in which the catalyst is washed. Changing the water from time to time speeds up the procedure.

The process may include reducing the calcined catalyst, eg by subjecting it to heat treatment under the influence of a reducing gas such as hydrogen.

It is usually desired that the resultant catalyst must comply geometrically with certain requirements in order to obtain a desired activity and/or selectivity, without the use of synthesis enhancing promotors, as hereinbefore described. Thus, for example, the catalyst may have a specified minimum pore size, typically a pore size of at least 12 nm. If the alumina carrier geometry is such that these geometric requirements in respect of the resultant catalyst will not be met, then the process may include pretreating the alumina carrier appropriately. Thus, the process may include pretreating the particulate alumina carrier or substrate prior to forming the slurry thereof with the water and the active component, to modify the average diameter of its pores, ie its pore size, and/or to modify its chemical phase.

This pretreatment may comprise chemically pretreating the carrier and/or precalcining it prior to the slurry formation. When the carrier is chemically pretreated, this may involve treating it with ammonia. In particular, the ammonia treatment may comprise forming a paste by admixing the alumina carrier with water; spraying ammonia onto the paste; optionally, spraying more water onto the ammoniated paste, with simultaneous mixing, eg kneading, of the paste; extruding the paste; drying it; and then calcining it. This calcination may be effected at a temperature between 200° C. and 1000° C., preferably between 500° C. and 900° C. An acid, such as acetic acid, may be added to the paste, if desired.

When the carrier is precalcined without chemical pretreatment thereof, as hereinbefore described, this calcination may also be effected at a temperature between 200° C. and 1000° C., preferably between 500° C. and 900° C. More particularly, the pretreatment may then comprise admixing the alumina carrier with water and an acid such as acetic acid; spraying additional water onto the mixture while mixing, eg kneading, it further; extruding the resultant paste; drying the extruded paste; and then effecting the calcination thereof. The water and acid initially mixed with the carrier may be in the form of dilute acid solution.

Naturally, the extrusion of the paste can be dispensed with if desired, eg if the resultant catalyst is to be used in a slurry bed reactor.

The alumina carrier or support may be that prepared by a spray-drying technique, provided that it has been subjected to the calcination temperature hereinbefore referred to, either during manufacture thereof, or subsequently during pretreatment thereof as hereinbefore described. Thus, a commercially available alumina support, such as the spray dried alumina support available from CONDEA Chemie GmbH of überseering 40, 22297 Hamburg, Germany.

The alumina carrier is thus characterized thereby that it is used in a relatively pure form, containing at most only minor proportions of impurities or undesired substances such as titania and/or, silica, and/or a minor proportion of a structural promotor as hereinbefore described. Furthermore, the process may be characterized thereby that the alumina carrier is the only carrier, ie that the alumina is not used in conjunction with other carriers or supports such as titania or silica.

The mass proportion of active component to alumina carrier in the slurry may be between 5:100 and 60:100, typically between 10:100 and 45:100.

The process may include adding to the slurry or to the impregnated uncalcined carrier or to the calcined catalyst, as a dopant, a minor proportion of an agent capable of enhancing the reducibility of the active component. The dopant may instead, or additionally, be added to the slurry which is formed when the calcined catalyst is reslurried as hereinbefore described. The dopant may comprise copper (Cu) and/or platinum (Pt). The mass proportion of the dopant, when present, to active component may be between 0.005:100 and 10:100, typically between 0.1:100 and 5.0:100 for copper, and between 0.01:100 and 0.3:100 for platinum.

The invention extends also to a Fischer-Tropsch catalyst, when produced by the process according to the invention.

The catalyst has high specific activity, and is suitable for the selective conversion of synthesis gas, utilizing Fischer-Tropsch reaction conditions in fixed or slurry catalyst beds, to high molecular weight saturated hydrocarbons, ie waxes.

BRIEF DESCRIPTION OF THE DRAWINGS

The invention will now be described in more detail with reference to the following non-limiting examples, and with reference to the accompanying drawings, in which.

DESCRIPTION OF THE PREFERRED EMBODIMENTS

Figure 1:
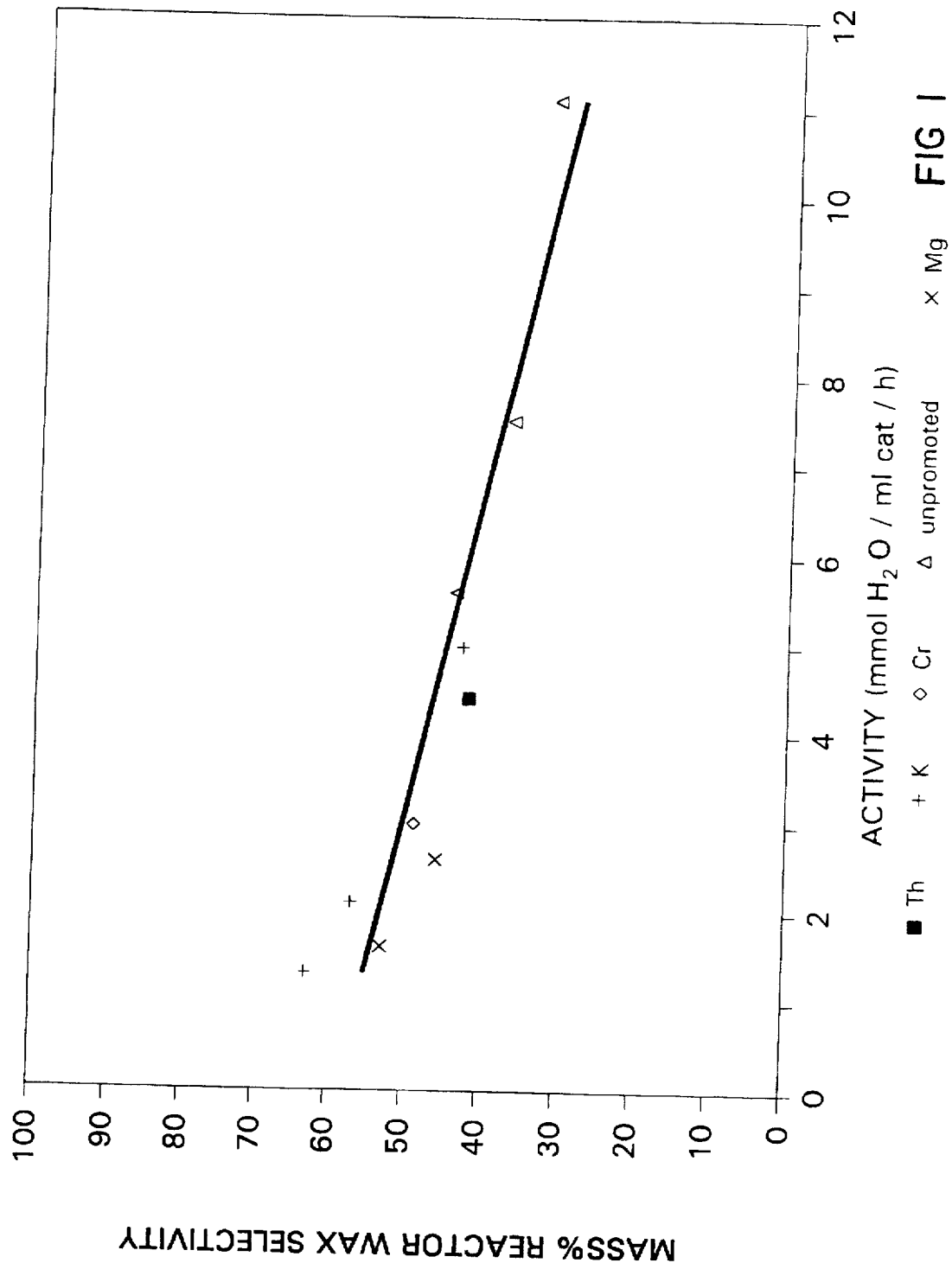
FIG. 1 shows a plot of wax selectivity vs activity in respect of the catalysts of Examples 1 to 8.

In the examples hereunder, a series of cobalt supported catalysts on alumina were prepared and tested for their activity in the conversion of synthesis gas into hydrocarbons.

Fixed Bed Tests

These tests were performed using 40 ml of catalyst. The catalyst was either crushed and sieved extrudates to particle sizes ranging from 1 mm to 1.7 mm, or spray dried to particle sizes ranging between 0.05 mm and 0.15 mm. A tubular reactor was used, and had an internal diameter of 1 cm and a length of 100 cm. The top part of the reactor was filled with an inert material to act as a pre-heater for the gas feed. The feed gas consisted of hydrogen and carbon monoxide in an $H_2/CO$ molar ratio of 2/1. The hydrogen and carbon monoxide accounted for about 84% (molar basis) of the feed. The other 16% was composed of inert gases, mainly methane (14.5%) and nitrogen (about 1%). The reactor was surrounded by an aluminium jacket which was electrically heated. The feed flow was controlled by means of Brooks mass flowmeters, and the Gas Hourly Space Velocity (GHSV) used in all the experiments was 4200 $h^{-1}$, based on total feed flow. The waxy products were collected in a condenser at about 18 bar and 130° C. This was followed by a condenser at about 18 bar and 20° C. for the liquid products.

Slurry Phase Tests

Between 10 and 30 g of catalyst, spray-dried to particle sizes ranging between 38 μm to 150 μm, was suspended in 300 ml molten wax and loaded in a CSTR with an internal volume of 500 ml. The feed gas consisted of hydrogen and carbon monoxide in a $H_2/CO$ molar ratio of 2/1. This reactor was electrically heated and sufficiently high stirrer speeds were employed so as to eliminate any gas-liquid mass transfer limitations. The feed flow was controlled by means of Brooks mass flow meters, and space velocities ranging between 1 and 3 $m^3_n/h/kg$ catalyst were used. GC analyses of the permanent gases as well as the volatile overhead hydrocarbons were used in order to characterize the product spectra.

All catalysts were reduced, prior to synthesis, in a fixed bed reactor at a pure hydrogen space velocity of 2 500 h$^{-1}$ and pressures ranging between 1 and 10 bar. The temperature was increased from room temperature to 350° C. to 400° C. at a rate of 1° C./min, after which isothermal conditions were maintained for 6 to 16 hours.

The catalysts were prepared according to the following examples:

EXAMPLE 1

50 g Alumina powder was added to 70 ml distilled water. To this 50 g Co(NO$_3$)$_2$.6H$_2$O was added. The mixture was kneaded thoroughly and extruded. The extrudates were dried in an oven for 2 to 3 hours at 100° C. and thereafter calcined at 350° C. for 16 hours. The alumina powder was that obtained from Degussa AG under the designation "Degussa Aluminium Oxide C".

EXAMPLE 2

In a similar manner to Example 1, a catalyst was prepared by impregnation, drying and calcining, except that 42.5 g, instead of 50 g, Co(NO$_3$)$_2$.6H$_2$O was added to the alumina and water mixture.

EXAMPLE 3

In a similar manner to Example 1, a catalyst was prepared but 37.5 g, rather than 50 g, Co(NO$_3$)$_2$.6H$_2$O was added to the alumina.

EXAMPLE 4

In a similar manner to Example 1, a catalyst was prepared, but 20 g Cr(NO$_3$)$_3$.9H$_2$O was added as a promoter.

EXAMPLE 5

50 g of the same alumina powder as used in Example 1, was added to 70 ml distilled water. To this mixture 25 g Co(NO$_3$)$_2$.6H$_2$O and 6.1 g Mg(NO$_3$)$_2$.6H$_2$O were added. The mixture was kneaded and extruded similarly to Example 1.

EXAMPLE 6

A catalyst was prepared in a similar manner to Example 1, but 0.35 g KNO$_3$ was added as a promoter.

EXAMPLE 7

A catalyst was prepared in a similar manner to Example 5, but 0.4 g KNO$_3$ was added in place of the Mg(NO$_3$)$_2$.6H$_2$O.

EXAMPLE 8

A catalyst was prepared in a similar manner to Example 1, but 4.9 g Th(NO$_3$)$_4$.5H$_2$O was added as a promoter.

The characteristics of the catalysts of Examples 1 to 8, as well as their performance in fixed bed Fischer-Tropsch synthesis, are presented in Table 1.

TABLE 1

| Catalyst Examples. | | | | Fischer-Tropsch fixed bed synthesis performance at 18 bar and a GHSV of 4 200 h$^{-1}$ | | |
|---|---|---|---|---|---|---|
| (Particle sizes varied | Active metal | Promoter | | Fischer-Tropsch | | |
| between 1.0 and 1.7 mm with a pore size of 24 nm) | content (g Co per 100 g Al$_2$O$_3$) | Element | Promotion level (expressed per 100 g Al$_2$O$_3$) | Reaction temperature (°C.) | activity expressed as m mol H$_2$O formed per ml catalyst per h | Mass % reactor wax selectivity (–C$_{19+}$) |
| 1 | 20 | — | — | 225 | 11.1 | 32 |
| 2 | 17 | — | — | 220 | 7.5 | 37 |
| 3 | 15 | — | — | 220 | 5.6 | 44 |
| 4 | 20 | Cr | 5.2 g | 220 | 3.0 | 49 |
| 5 | 10 | Mg | 1.2 g | 220 | 2.6 | 46 |
| 5 | 10 | Mg | 1.2 g | 215 | 1.6 | 53 |
| 6 | 20 | K | 0.3 g | 220 | 5.0 | 44 |
| 7 | 10 | K | 0.3 g | 220 | 2.1 | 57 |
| 7 | 10 | K | 0.3 g | 215 | 1.3 | 63 |
| 8 | 20 | Th | 4.0 g | 218 | 4.4 | 42 |

It can thus be seen that there is a strong correlation between the wax selectivity (defined here as the fraction of hydrocarbons condensed at 130° C. at 18 bar) and the activity of the catalyst. This correlation is independent of the nature of the promoter and also independent of the addition of a promoter. This is more clearly indicated in FIG. 1 which graphically shows the data of Table 1.

Additional supported cobalt catalysts were prepared according to the following procedure in order to cover a range of pore sizes.

EXAMPLE 9

A catalyst was prepared in a similar manner to Example 1 but 12.5 g Mg(NO$_3$)$_2$.6H$_2$O was added as a promoter.

EXAMPLE 10

A catalyst was prepared in a similar manner to Example 5 except that 4.0 g Zr(IV)acetylacetonate was added in the place of the Mg(NO$_3$)$_2$.6H$_2$O.

EXAMPLE 11

A catalyst was prepared in a similar manner to Example 1, but 0.85 g KNO$_3$ was added as a promoter.

These catalysts were dried, calcined and tested for their fixed bed synthesis behaviour in a similar fashion to the catalysts of Examples 1 to 8. The physical characteristics and the catalytic activity of the catalysts are presented in table 2.

TABLE 2

| Catalyst Examples [Particle sizes varied between 1.0 and 1.7 mm] | Active metal content (g Co per 100 g $Al_2O_3$) | Promoter | | Pore size (nm) | Fischer-Tropsch fixed bed synthesis performance at 18 bar, 220° C., and a GHSV of 4 200 $h^{-1}$ | |
|---|---|---|---|---|---|---|
| | | Element | Promotion level (expressed per 100 g $Al_2O_3$) | | Fischer-Tropsch activity expressed as m mol $H_2O$ formed per ml catalyst per h | Mass % reactor wax selectivity (~$C_{19+}$) |
| 9 | 20 | Mg | 2.4 g | 21.5 | 2.5 | 24 |
| 10 | 10 | Zr | 1.5 g | 22.5 | 2.1 | 30 |
| 5 | 10 | Mg | 1.2 g | 24.0 | 2.6 | 46 |
| 7 | 10 | K | 0.3 g | 24.3 | 2.1 | 57 |
| 11 | 20 | K | 0.7 g | 25.9 | 2.3 | 61 |

Figure 2:
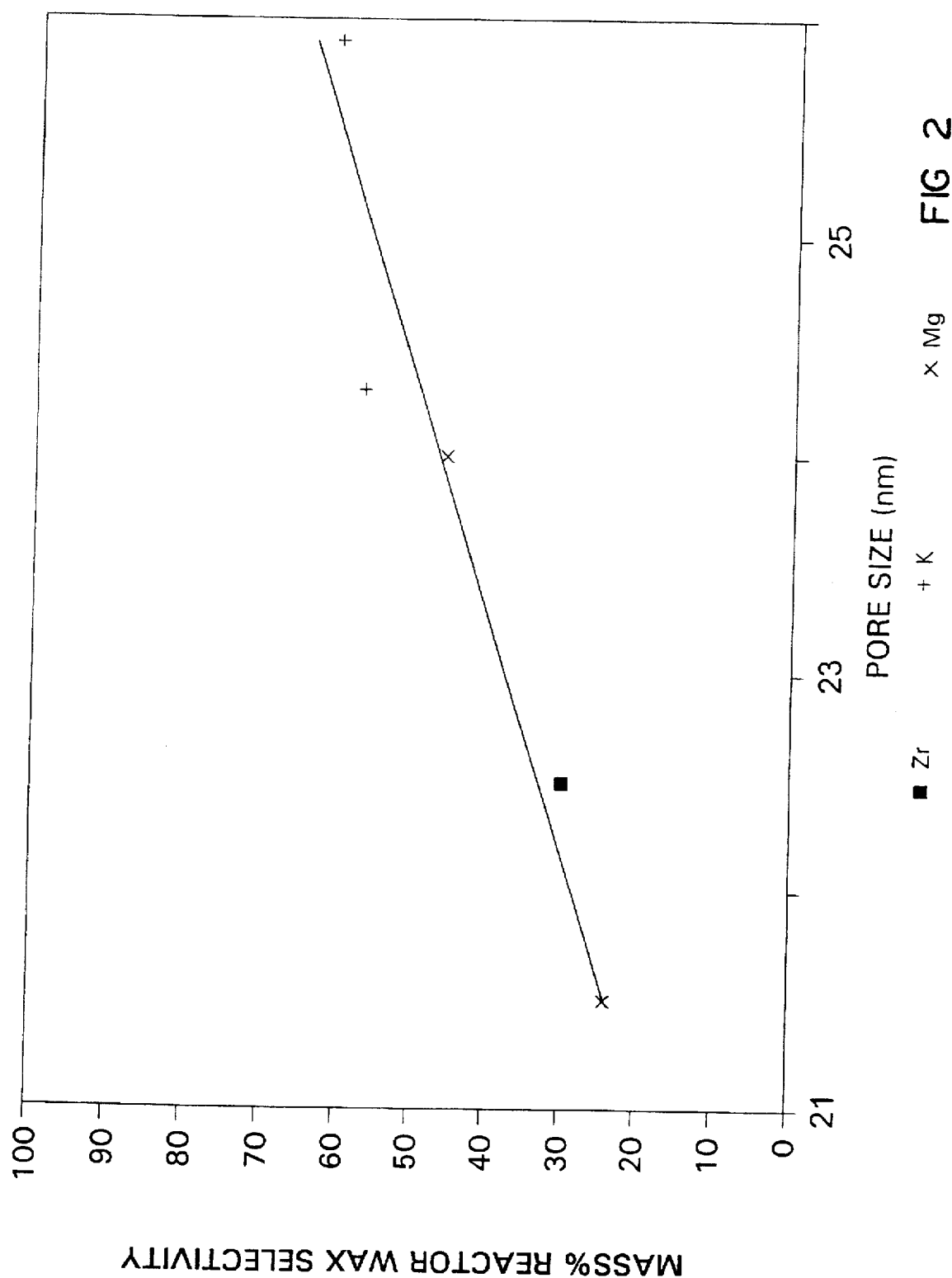
FIG. 2 shows a plot of wax selectivity vs pore size in respect of the catalysts of Examples 5, 7, 9, 10 and 11.

From Table 2 it can thus be seen that for a given activity (ie ~2 m mol $H_2O$/ml cat/h), reactor wax selectivity is a strong function of average catalyst pore size. This relationship is independent of the type of promoter added. This is more clearly illustrated in FIG. 2, which graphically illustrates the results shown in Table 2.

In Examples 1 to 11, use was made of fumed $Al_2O_3$ which was co-extruded with the catalytically active components. An alternative approach is to extrude (or spray dry) and calcine the $Al_2O_3$ support separately as a first preparation step, prior to impregnation with the active component(s). This procedure allows for more freedom with respect to tailoring of the support geometry.

For this application, precipitated $Al_2O_3$, supplied by Condea Chemie GmbH, under their designations 'Pural SB alumina', 'Puralox SCCa 5/150, or Puralox HP 5/180' was used. The average pore size of the support was increased by the following pretreatment techniques: by calcination and/or by chemical treatment with an alkaline compound such as ammonia. Examples 12 to 35 thus are directed to pretreated supports.

EXAMPLE 12

125 ml acetic acid diluted with 1.7 l distilled water was added to 2 kg Pural SB alumina powder obtained from Condea. Another 1.2 l water was sprayed on while kneading the mixture. The alumina was extruded, dried at 120° C. for 12 hours, and calcined at 600° C. for 16 hours, to produce a pretreated support.

EXAMPLE 13

A support was prepared in a similar manner to the support of Example 12, but using a calcination temperature of 700° C., instead of 600° C.

EXAMPLE 14

A support was prepared in a similar manner to the support of Example 12, but using a calcination temperature of 800° C., instead of 600° C.

EXAMPLE 15

125 ml acetic acid diluted with 1.4 l distilled water was added to 2 kg Pural SB alumina in a mixer. 250 ml Ammonia (12.5 vol %) was sprayed onto this alumina paste. A further 1.2 l water was sprayed onto the alumina while kneading the paste. The alumina was then extruded, dried at 120° C. for 12 hours, and calcined at 600° C. for 16 hours.

EXAMPLE 16

A support was prepared in a similar manner to the support of Example 15, but using a calcination temperature of 700° C., instead of 600° C.

EXAMPLE 17

A support was prepared in a similar manner to the support of Example 15, but using a calcination temperature of 800° C., instead of 600° C.

EXAMPLE 18

19 ml $C_3COOH$ was diluted to 210 ml with distilled water. 20 g of $Zr(NO_3)_4.5H_2O$ was dissolved into this solution. This solution was then sprayed onto 300 g Pural SB alumina while mixing in a mixer. 180 ml of a 1.8 vol % ammonia solution was then sprayed onto the alumina while kneading the paste. The paste was then extruded, dried at 120° C. for 2 hours and calcined at 750° C. for 16 hours.

EXAMPLE 19

A solution of 100 g 4 $Mg(CO_3).Mg(OH_2).4$ $H_2O$, 160 ml $CH_3COOH$ and 150 ml distilled water was sprayed onto 300 g Pural SB alumina while mixing it in a mixer. This was then followed by spraying 220 ml of 12.5 vol % ammonia onto the kneading mixture. After extruding the paste, the extrudates were dried at 120° C. for 2 hours, and calcined at 750° C. for 16 hours.

EXAMPLE 20

A solution of 30 g $Zr(NO_3)_4.5H_2O$ in 210 ml distilled water was sprayed onto 300 g of Pural SB alumina while mixing in a mixer. While kneading this mixture, 180 ml of a 3.5 vol % ammonia solution was sprayed onto it. The paste was then extruded, dried at 120° C. for 2 hours, and calcined at 750° C. for 16 hours.

EXAMPLE 21

A support was prepared in a similar manner to the support of Example 18, but instead of 20 g $Zr(NO_3)_4.5H_2O$, 30 g $Mg(NO_3)_2.6H_2O$ was used.

EXAMPLE 22

A support was prepared in a similar manner to the support of Example 18, but instead of 20 g $Zr(NO_3)_4.5H_2O$, 9 g $KNO_3$ was used.

EXAMPLE 23

A support was prepared in a similar manner to the support of Example 18, but instead of 20 g $Zr(NO_3)_4.5H_2O$, 20 g $Mn(NO_3)_2.4H_2O$ was used.

EXAMPLE 24

Puralox SCCa 5/150 support was calcined at 750° C. for 16 hours.

EXAMPLE 25

Puralox SCCa 5/150 support was calcined at 800° C. for 16 hours.

EXAMPLE 26

Puralox SCCa 5/150 support was calcined at 900° C. for 16 hours.

EXAMPLE 27

Puralox SCCa 5/150 support was calcined at 1 000° C. for 16 hours.

EXAMPLE 28

Puralox HP 5/180 support was calcined at 600° C. for 16 hours.

EXAMPLE 29

Puralox HP 5/180 support was calcined at 70020 C. for 16 hours.

EXAMPLE 30

Puralox HP 5/180 support was calcined at 750° C. for 16 hours.

EXAMPLE 31

Puralox HP 5/180 support was calcined at 800° C. for 16 hours.

EXAMPLE 32

Puralox HP 5/180 support was calcined at 900° C. for 16 hours.

EXAMPLE 33

Puralox HP 5/180 support was calcined at 1 000° C. for 16 hours.

EXAMPLE 34

Puralox HP 5/180 support was calcined at 1 100° C. for 16 hours.

EXAMPLE 35

A support was prepared in a similar manner to the support of Example 15, but using a calcination temperature of 750° C., instead of 600° C.

The physical properties of the pretreated supports of Examples 12 to 35 are given in Table 3.

TABLE 3

| Example | Calcination Temperature °C. | BET area $m^2/g$ | Pore Volume ml/g | Average pore size nm |
|---|---|---|---|---|
| 12 | 600 | 213 | 0.46 | 8.6 |
| 13 | 700 | 193 | 0.46 | 9.5 |
| 14 | 800 | 165 | 0.44 | 10.6 |
| 15 | 600 | 211 | 0.54 | 10.2 |
| 16 | 700 | 192 | 0.54 | 11.2 |
| 17 | 800 | 161 | 0.52 | 12.9 |
| 18 | 750 | 201 | 0.48 | 9.6 |
| 19 | 750 | 157 | 0.46 | 11.2 |
| 20 | 750 | 143 | 0.44 | 12.3 |
| 21 | 750 | 185 | 0.51 | 10.9 |
| 22 | 750 | 189 | 0.50 | 10.5 |
| 23 | 750 | 198 | 0.49 | 9.9 |
| 24 | 750 | 155 | 0.48 | 12.5 |
| 25 | 800 | 143 | 0.50 | 12.9 |
| 26 | 900 | 134 | 0.48 | 15.0 |
| 27 | 1 000 | 100 | 0.35 | 16.1 |
| 28 | 600 | 180 | 0.65 | 14.4 |
| 29 | 700 | 169 | 0.65 | 15.5 |
| 30 | 750 | 172 | 0.65 | 12.5 |
| 31 | 800 | 133 | 0.64 | 19.2 |
| 32 | 900 | 116 | 0.61 | 21.1 |
| 33 | 1 000 | 92 | 0.52 | 21.9 |
| 34 | 1 100 | 60 | 0.25 | 16.0 |
| 35 | 750 | 130 | 0.55 | 16.0 |

Increasing calcination temperature thus decreased the surface area of the supports. This effect was very similar for both types of support, ie with and without ammonia treatment.

The average pore size increased with an increase in the calcination temperature. The catalysts prepared with ammonia show a higher average pore size than the catalysts prepared in the absence of ammonia.

The supports of Examples 12 to 35 were impregnated with cobalt to determine the effect of their average pore size on wax selectivity. The following procedure was used:

50 g of support was added to a solution of 50 g Co($N_3$)$_2$.6$H_2O$ and 0.05 g Pt($NH_3$)$_4$ ($NO_3$)$_2$ in 50 to 70 ml distilled water. The water was evaporated at 70° C. under vacuum in a rotary evaporator. The catalyst was calcined at 350° C. in a counter-current airflow for 6 hours.

The average pore sizes as well as reactor wax selectivities, as obtained in the tubular fixed bed reactor used in Examples 1 to 11, are shown in Table 4.

TABLE 4

| 20 Co/100 Al$_2$O$_3$ catalysts (Particle sizes varied between 0.1 and 1.7 mm with pore volumes between 0.32 and 0.44 ml/g) Example | Support Example | Promoter Element | Promotion level (expressed per 100 g Al$_2$O$_3$) | Average pore size (nm) | Mass % liquid hydrocarbons, drained as wax and oil (ie - C$_5$+) as measured during fixed bed reactor tests Reaction Conditions: Temperature 200–208° C. Pressure 18 bar GHSV 2500–3500 h$^{-1}$ Vol % CO conversion 10–20 |
|---|---|---|---|---|---|
| 36 | 12 | — | — | 7.5 | 44 |
| 37 | 13 | — | — | 8.0 | 52 |
| 38 | 14 | — | — | 8.9 | 52 |
| 39 | 15 | — | — | 8.6 | 57 |
| 40 | 16 | — | — | 9.7 | 60 |
| 41 | 17 | — | — | 10.7 | 63 |
| 42 | 18 | Zr | 1.4 g | 9.0 | 46 |
| 43 | 19 | Mg | 8.6 g | 10.1 | 63 |
| 44 | 20 | Zr | 2.1 g | 10.4 | 54 |
| 45 | 21 | Zr | 0.9 g | 9.5 | 53 |
| 46 | 22 | K | 1.2 g | 9.0 | 44 |
| 47 | 23 | Mn | 1.5 g | 9.4 | 40 |
| 48 | 24 | — | — | 11.0 | 75 |
| 49 | 25 | — | — | 11.3 | 74 |
| 50 | 26 | — | — | 13.1 | 80 |
| 51 | 27 | — | — | 13.7 | 68 |
| 52 | 28 | — | — | 13.6 | 79 |
| 53 | 29 | — | — | 14.1 | 81 |
| 54 | 30 | — | — | 15.9 | 81 |
| 55 | 31 | — | — | 17.0 | 79 |
| 56 | 32 | — | — | 17.7 | 76 |
| 57 | 33 | — | — | 18.7 | 77 |
| 58 | 34 | — | — | 17.3 | 81 |
| 59 | 35 | — | — | 10.7 | 58 |

From Table 4 it can be seen that for a given activity, the reactor wax selectivity is a function of average catalyst pore size, independent of the type of promoter used (ie Zr, Mg, Mn, or K). This is more clearly illustrated in FIG. 3, which summarizes the results shown in Table 4.

These tubular fixed bed synthesis Examples thus show that the main variables affecting wax selectivity from a cobalt based Fischer-Tropsch catalyst are the average pore size diameter of the support or carrier and the intrinsic catalyst activity.

Figure 3:
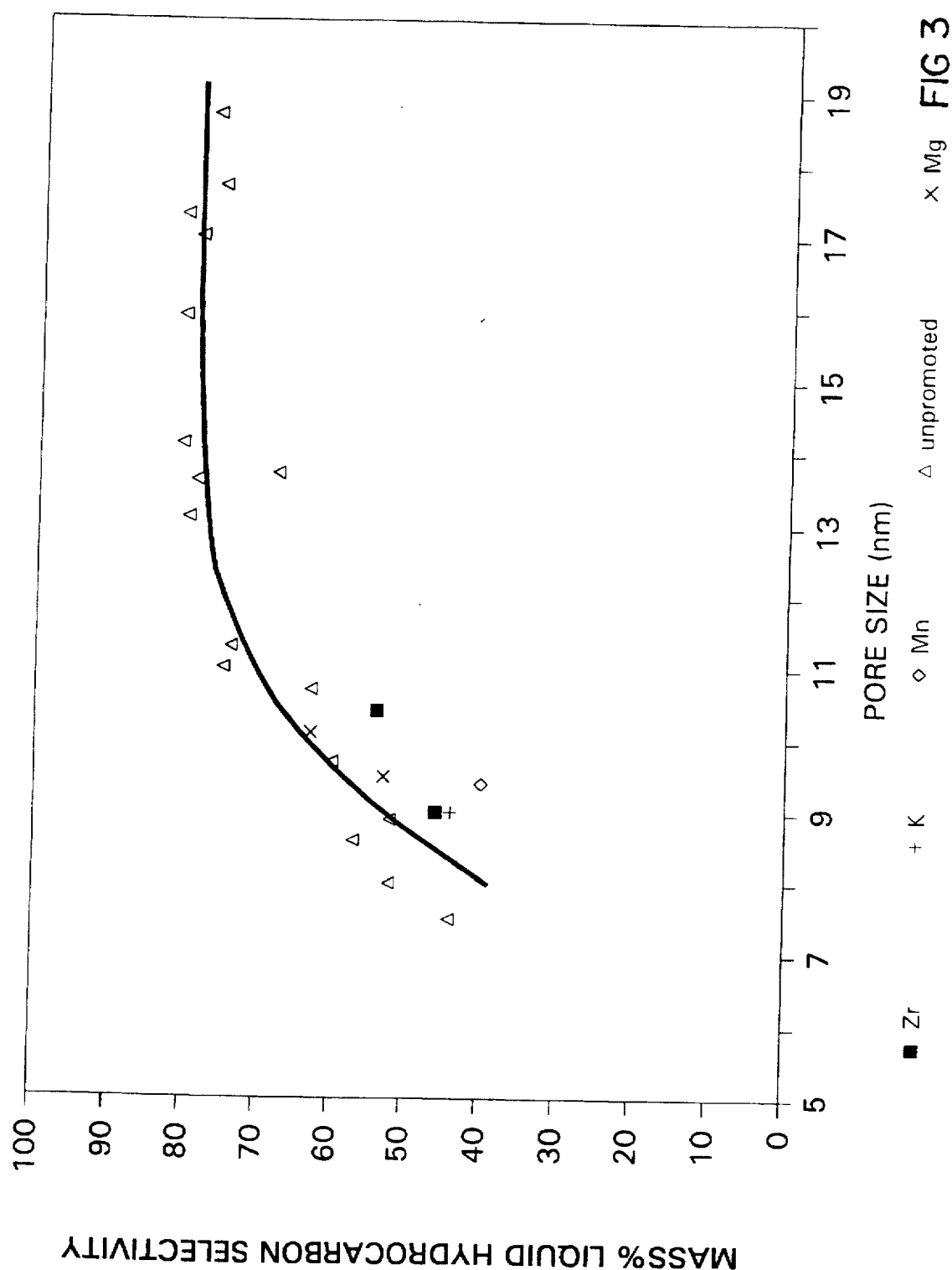
FIG. 3 shows a plot of wax selectivity vs pore size in respect of the catalysts of Examples 36 to 59.

In Examples 60 to 65 hereunder, commercially available spraydried and calcined Al$_2$O$_3$ Puralox SCCa 5/150 was used. This material was calcined at a temperature between 600° C. and 700° C. during manufacture thereof. This Al$_2$O$_3$ support material had a pore size of 12.5 nm which, as seen in FIG. 3, is optimal from a wax selectivity and catalyst activity point of view. All the physical properties of this support material are listed in Table 5.

TABLE 5

| Physical property | Al$_2$O$_3$, Puralox SCCa 5/150 (used as selected support for the preparation of slurry phase Fischer-Tropsch catalysts) |
|---|---|
| Pore size | 12.5 nm |
| Surface area | 150 m$^2$/g |
| Pore volume | 0.5 ml/g |
| Particle size distribution | 45–150 μm |
| Crystalline phase | Gamma |

Six catalyst samples were prepared with this support.

EXAMPLE 60

40 g Co(NO$_3$)$_2$.6H$_2$O was dissolved in 50 ml distilled water, and 50 g Al$_2$O$_3$ Puralox SCCa 5/150 was suspended in this solution. This slurry was treated for ~2.5 hours at 75° C. and 2 to 5 kPa in a rotary evaporator to impregnate the alumina carrier and to dry the impregnated carrier. The dried impregnated carrier was dried further and calcined at 230° C. for 2 hours in an air flow of 1.5 l$_n$/min. The resultant calcined sample was re-slurried in a solution that was made up by having dissolved 35 g Co(NO$_3$)$_2$.6H$_2$O and 50 mg Pt(NH$_3$)$_4$(NO$_3$)$_2$ in 50 ml of distilled water. This slurry was again vacuum treated for ~2.5 hours at 75° C. and 2 to 5 kPa until free flowing in a rotary evaporator. The dried impregnated carrier was calcined at 230° C. for 2 hours in an air flow of 1.5 l$_n$/min.

EXAMPLE 61

40 g Co(NO$_3$)$_2$.6H$_2$O was dissolved in 50 ml distilled water, and 50 g Al$_2$O$_3$ Puralox SCCa 5/150 was suspended in this solution. This slurry was treated for ~2.5 hours at 75° C. and 2 to 5 kPa in a rotary evaporator to impregnate the alumina carrier and to dry the impregnated carrier. The dried impregnated carrier was calcined at 380° C. for 5 hours in an air flow of 1.5 l$_n$/min. The calcined sample was re-slurried in a solution that was made up by having dissolved 35 g Co(NO$_3$)$_2$.6H$_2$O in 50 ml distilled water. This slurry was again vacuum treated for ~2.5 hours at 75° C. and 2 to 5 kPa in a rotary evaporator, followed by calcination at 380° C. for 5 hours in an air flow of 1.5 l$_n$/min. The calcined sample was re-slurried in a solution that was made up by having dissolved 0.8 g Ru (III) acetylacetonate in 50 ml acetone. This slurry was again vacuum treated, ie dried, until free flowing at 75° C. and 2 to 5 kPa in a rotary evaporator, followed by a final calcination step at 330° C. for 4 hours in an air flow of 1.5 $l_n$/min.

EXAMPLE 62

40 g Co(NO$_3$)$_2$.6H$_2$O and 1.2 g perrhenic acid (HReO$_4$) was dissolved in 50 ml distilled water, and 50 g Al$_2$O$_3$ Puralox SCCa 5/150 was suspended in this solution. This slurry was vacuum treated for ~2.5 hours at 75° C. in a rotary evaporator to impregnate the alumina carrier and to dry the impregnated carrier, followed by calcination at 350° C. for 5 hours in an air flow of 1.5 $l_n$/min. This calcined sample was re-slurried in a solution that was made up by having dissolved 35 g Co(NO$_3$).6H$_2$O and 0.8 g perrhenic acid in 50 ml distilled water. This slurry was again vacuum dried for ~2.5 hours at 75° C. until free flowing in a rotary evaporator, followed by calcination at 350° C. for 5 hours in an air flow of 1.5 $l_n$/min.

EXAMPLE 63

29.6 g Co(NO$_3$)$_2$.6H$_2$O and 30 mg Pt(NH$_3$)$_4$(NO$_3$)$_2$ was dissolved in 50 ml distilled water, and 50 g Puralox SCCa 5/150 was suspended in this solution. The slurry was vacuum treated for ~2.5 hours at 75° C. and 2 to 5 kPa in a rotary evaporator to impregnate the alumina carrier and to dry the impregnated carrier. The dried impregnated carrier was calcined at 230° C. for 2 hours in an air flow of 1.5 $l_n$/min. The calcined sample was re-slurried in a solution that was made up by having dissolved 19.8 g Co(NO$_3$)$_2$.6H$_2$O and 20 mg Pt(NH$_3$)$_4$(NO$_3$)$_2$ in 50 ml of distilled water. This slurry was again vacuum dried for ~2.5 hours at 75° C. and 2 to 5 kPa until free flowing in a rotary evaporator. The dried impregnated sample was calcined at 230° C. for 2 hours in an air flow of 1.5 $l_n$/min.

EXAMPLE 64

This Example was similar to Example 61 with the following differences:

1st impregnation: 30 g Co(NO$_3$)$_2$.6H$_2$O was used instead of 40 g Co(NO$_3$)$_2$.6H$_2$O 2nd impregnation: 20 g Co(NO$_3$)$_2$.6H$_2$O was used instead of 35 g. Co(NO$_3$)$_2$.6H$_2$O 3rd impregnation: 0.55 g Ru (III) acetylacetonate was used instead of 0.8 g Ru (III) acetylacetonate Thus, Examples 60 to 64 were prepared by means of slurry impregnation, ie impregnation solution in excess of the total available alumina carrier pore volume.

EXAMPLE 65

26 kg Al$_2$O$_3$ Puralox SCCa 5/150 was incipient impregnated with a 12.5 l aqueous solution containing 13.9 kg Co(NO$_3$)$_2$.6H$_2$O and 8.6 g Pt(NH$_3$)$_4$(NO$_3$)$_2$. This impregnated sample was dried at 80° C. for 10 hours in an air flow of 40 $l_n$/min, followed by calcination at 240° C. for 4 hours in an air flow of 250 $l_n$/min. In incipient impregnation, the volume of the impregnation solution used, ie the aqueous solution referred to above, is equal to the pore volume of the alumina carrier.

A second incipient impregnation step followed during which this sample was impregnated with 11.3 l of an aqueous solution containing 12.1 kg Co(NO$_3$)$_2$.6H$_2$O and 8.6 g Pt(NH$_3$)$_4$(NO$_3$)$_2$. Drying and calcination was performed similarly to the first step.

A third and final incipient impregnation step followed during which this sample was impregnated with 13.2 l of an aqueous solution containing 14.2 kg Co(NO$_3$)$_2$.6H$_2$O and 8.6 g Pt(NH$_3$)$_4$(NO$_3$)$_2$, followed by the same drying and calcination steps as described above.

The preparation method of Example 60 was successfully scaled up to pilot plant scale, more or less on the same scale as that of Example 65. Proper vacuum drying proved to be an important parameter in the case of the scaled up version of the slurry impregnation option. The final moisture content of this dried impregnated catalyst should be less than ~20 mass %. This permits calcination where the dried impregnated catalyst is first passed through a counter current air drier (residence time of ~1 min) set at 180° C., falling directly into a tubular calciner unit set at 250° C. The air flow through the calciner was set at ~8 dm$_n^3$/kg cat/min at a superficial velocity of ~5 cm/s. Proper calcination required calcination periods in excess of 3 hours, preferably ~6 hours.

Examples 60, 63 and 65 were "unpromoted". Small quantities of Pt were added to assist with catalyst reduction. These quantities could vary between 0.03 g Pt and 0.08 g Pt per 100 g Al$_2$O$_3$, and could be co-impregnated throughout all the impregnation steps (eg Example 65) or concentrated in the final impregnation step (eg Example 60).

The slurry phase Fischer-Tropsch activities of catalyst Examples 60 to 65 are listed in Table 6.

TABLE 6

| | | Promoter | | Fischer-Tropsch slurry phase synthesis performance at 220° C., 20 bar, and at a space velocity of 2.0 m$_n^3$/h/kg catalyst. (feed gas: 33.3 vol % CO and 66.7 vol % H$_2$) | | | |
|---|---|---|---|---|---|---|---|
| | Active metal | | Promotion level | After 100 hours on line | | After 400 hours on line | |
| Catalyst Sample | Content (g Co per 100 g Al$_2$O$_3$) | Element | (expressed per 100 g Al$_2$O$_3$) | Vol % CO conversion | Productivity kg HC/kg Cat/h | Vol % CO conversion | Productivity kg HC/kg Cat/h |
| 60 | 30 | Pt | 0.05 g | 87 | 0.349 | 84 | 0.336 |
| 61 | 30 | Ru | 0.41 g | 77 | 0.307 | 70 | 0.281 |
| 62 | 30 | Re | 3.0 g | 70 | 0.281 | NA | NA |
| 63 | 20 | Pt | 0.05 g | 73 | 0.291 | 63 | 0.250 |
| 64 | 20 | Ru | 0.28 g | 73 | 0.288 | 63 | 0.252 |
| 65 | 31 | Pt | 0.05 g | 77 | 0.310 | NA | NA |

The following conclusions are evident from Table 6:

Ru or Re promotion, which can be expensive at the required levels, does not result in enhanced specific Fischer-Tropsch activities at a cobalt content of ~20 mass % (ie 30 g Co/100 g $Al_2O_3$).

Applying a reported cobalt based Fischer-Tropsch kinetic equation, such as:

$$r_{FT}=(k_{FT}P_{h_2}P_{CO})/(1+\beta.P_{CO})^2,$$

shows that intrinsic activity is linearly proportional to the cobalt content of a m Co/0.05 Pt/100 $Al_2O_3$ catalyst ($Al_2O_3$ Puralox SCCa 5/150) up to a level of m=30 (ie constant cobalt utilization). At higher cobalt loadings (ie m>30) cobalt utilization is diminished.

In the preparation of the m Co/0.05 Pt/100 $Al_2O_3$ catalyst, the method of slurry impregnation (eg Example 60) is preferred with respect to incipient wetness impregnation (eg Example 65). The former impregnation method resulting in a catalyst with an intrinsic Fischer-Tropsch activity level ~1.35 times higher than the latter.

A selectivity investigation on this preferred cobalt slurry phase catalyst (ie Example 60) was performed and modelled. Table 7 provides an example of best fitted Schulz-Flury modelled selectivities of this catalyst, at representative synthesis conditions.

TABLE 7

| % CO conversion at 220° C. and 20 bar with a feed composed of | Mass % selectivities of the catalyst sample 36 after 400 hours on line | | | | |
|---|---|---|---|---|---|
| 67 vol % $H_2$ and 33 vol % CO | Fuelgas $C_1$–$C_2$ | LPG $C_3$–$C_4$ | Gasoline $C_5$–$C_{11}$ | Diesel $C_{12}$–$C_{18}$ | Wax $C_{19+}$ |
| 94 | 28 | 18 | 34 | 14 | 6 |
| 84 | 13 | 12 | 32 | 21 | 22 |
| 68 | 8 | 9 | 26 | 21 | 36 |
| 54 | 6 | 7 | 24 | 21 | 42 |
| 44 | 6 | 7 | 22 | 20 | 45 |
| 37 | 5 | 6 | 22 | 20 | 47 |
| 32 | 5 | 6 | 21 | 20 | 48 |
| 28 | 5 | 6 | 21 | 19 | 49 |
| 23 | 5 | 6 | 20 | 19 | 50 |
| 18 | 4 | 6 | 20 | 19 | 51 |
| 15 | 4 | 6 | 20 | 19 | 51 |

Figure 4:
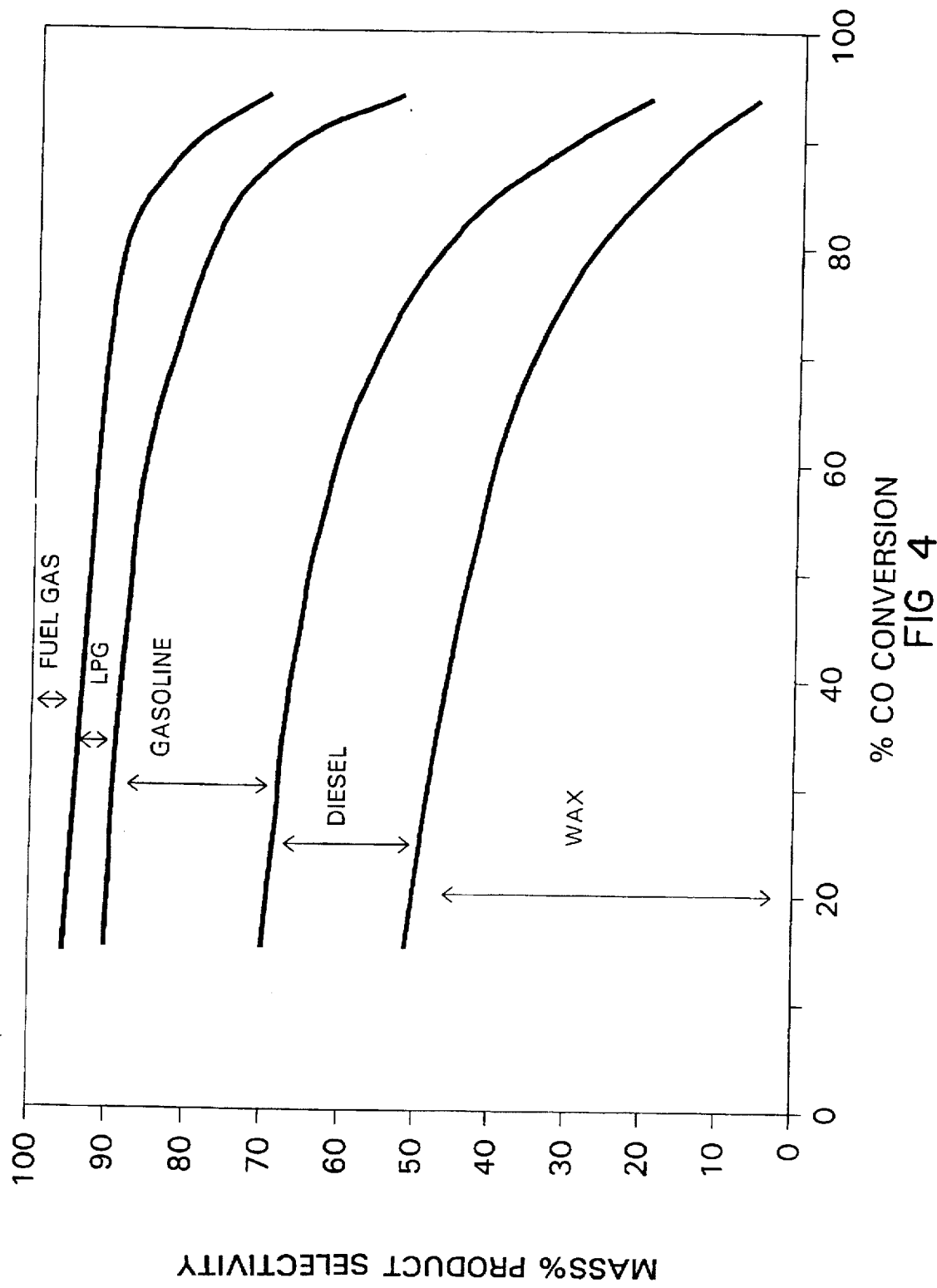
FIG. 4 shows a plot of percentage CO conversion vs selectivity in respect of the catalysts of Example 60.

A graphical illustration of table 7 is presented in FIG. 4, which underlines the dependence between activity and selectivity, as also deduced from FIG. 1 for the fixed bed application.

With respect to wax quality, slurry impregnation method (eg is described in the preparation of Example 60) is superior to the incipient wetness impregnation option (eg as described in the preparation of Example 65).

The reaction wax produced by catalyst Example 65, contained suspended sub-micron $Co_3O_4$ particles, at cobalt concentration level of ~100 ppm, which could not be removed by means of filtration through a Whatmans 42 filter paper. This also impacted negatively on the wax colour, and an undesirable saybolt colour of −16 (ie darkest indicator) was determined for the filtered reactor wax. The origin of these sub-micron $Co_3O_4$ contaminant, was traced back to the presence of a clearly defined shell containing Co and no Al (~1 µm thick as observed through a SEM investigation), uniformly encapsulating the spray-dried $\gamma$ $Al_2O_3$ spheres.

A thorough washing of the calcined catalyst Example 65, successfully removed this unwanted cobalt enriched material, without exerting any influence on the specific Fischer-Tropsch activity. This is despite of the fact that up to ~8% of the original cobalt content could be washed out.

Details of water washing procedure:

Experience gained during the washing of ~5 kg of catalyst Example 65 (ie after the final calcination step and before reduction), has shown that at least 25 l of water is required per kg of catalyst.

Procedures that must be adhered to during the washing are:

The water must be agitated to a limited degree, and this can be achieved through boiling.

Changing water from time to time speeds up the procedure, eventually becoming clear, thus the recommended 25 l per kg of catalyst.

The unwanted situation of wax contamination has been proved to be almost absent in the case of slurry phase impregnated catalysts (eg sample 60), viz: catalysts with more homogeneous cobalt distribution throughout the particles, encapsulated by a far less pronounced cobalt oxide shell, is produced.

A water washing step is, however, still to be recommended in order to ensure a high quality wax. Wax produced by a washed slurry impregnated 30 Co/0.05 Pt/100 $Al_2O_3$ catalyst contained only 1 to 3 ppm cobalt resulting in a saybolt colour of 10, after filtration through a Whatmans 42 filter paper.

Thus, very active cobalt based (fixed bed and slurry phase) Fischer-Tropsch catalysts can be prepared in a relatively inexpensive and easy manner, eg no expensive wax selectivity promoters are required in accordance with the invention.

We claim:

1. A process for preparing a Fischer-Tropsch catalyst, which process comprises subjecting a slurry comprising a particulate alumina carrier, water and an active component selected from the group consisting in cobalt (Co), iron (Fe) and mixtures thereof, to a sub-atmospheric pressure environment, thereby to impregnate the alumina carrier with the active component;

drying the impregnated carrier under a sub-atmospheric pressure environment; and calcining the dried impregnated carrier, thereby to obtain the Fischer-Tropsch catalyst.

2. A process according to claim 1, wherein the sub-atmospheric pressure environment during the impregnation is at a pressure less than 20 kPa(a).

3. A process according to claim 1, wherein he sub-atmospheric pressure environment during the drying is at a pressure less than 20 kPa(a).

4. A process according to claim 1, wherein the impregnation and drying in the sub-atmospheric pressure environments is effected in a single step, so that the impregnation is effected while the drying takes place.

5. A process according to claim 1, wherein the drying in the sub-atmospheric pressure environment is continued until the moisture content of the impregnated carrier is below 20% by mass, whereafter the impregnated carrier is dried further under non-sub-atmospheric pressure conditions by passing a drying medium in co-current or counter-current fashion over the impregnated carrier at a drying temperature between 100° C. and 180° C.

6. A process according to claim 1, which includes adding to the slurry or to the impregnated uncalcined carrier, as a dopant, a minor proportion of an agent capable of enhancing the reducibility of the active component.

7. A process according to claim 6, wherein the dopant comprises copper (Cu) and/or platinum (Pt), and wherein the mass proportion of the dopant to active component is between 0.005:100 and 10:100.

8. A process according to claim 1, wherein the calcined catalyst is re-slurried with water together with at least one of the following: the active component, another active component, or, as a dopant, a minor proportion of an agent capable of enhancing the reducibility of the active component, with the resultant impregnated carrier then again being subjected to drying and calcination.

9. A process according to claim 1, wherein the calcination of the dried impregnated carrier is effected at a temperature below 350° C.

10. A process according to claim 1, which includes washing the catalyst with a washing medium, to remove unwanted surface contaminants therefrom.

11. A process according to claim 1, which includes forming the slurry by dissolving a water soluble compound of the active component in water, prior to forming the slurry with the alumina carrier, and forming of the slurry by intimately admixing the alumina carrier and the solution of the active component compound.

12. A process according to claim 11, which includes pretreating the particulate alumina carrier prior to forming the slurry thereof with the water and the active component, to modify the average diameter of its pores and/or to modify its chemical phase, by chemically pretreating the carrier and/or precalcining the carrier prior to the slurry formation.

13. A process according to claim 1, wherein the mass proportion of active component to alumina carrier in the slurry is between 5:100 and 60:100.

14. A Fischer-Tropsch catalyst, when produced by the process according to claim 1.

15. A process according to claim 1, wherein no promoter to enhance the activity of the resultant catalyst or to modify its selectivity, and which is selected from the group consisting of potassium (K), chromium (Cr), magnesium (Mg), zirconium (Zr), ruthenium (Ru), thorium (Th), hafnium (Hf), cerium (Ce), rhenium (Re), uranium (U), vanadium (V), titanium (Ti), manganese (Mn), nickel (Ni), molybdenum (Mo), wolfram (W), lanthanum (La), palladium (Pd), uranium (U), praseodymium (Pr), neodymium (Nd) and other elements from groups IA or IIA of the periodic table of the elements, is added to the slurry or to the impregnated carrier.

16. A process according to claim 1, wherein the particulate alumina carrier has pores having a minimum pore diameter of 12 nm and/or has been chemically pretreated with ammonia and/or has been calcined at a temperature between 200° C. and 1000° C.

17. A process for preparing a Fischer-Tropsch catalyst, which process comprises subjecting a slurry comprising a particulate alumina carrier having pores with a minimum pore diameter of at least 12 nm and/or having been chemically pretreated with ammonia and/or having been calcined at a temperature between 200° C. and 1000° C., water and an active component selected from the group consisting of cobalt (Co), iron (Fe) and mixtures thereof, to a sub-atmospheric pressure environment, thereby to impregnate the alumina carrier with the active component;

drying the impregnated carrier under a sub-atmospheric pressure environment; and calcining the dried impregnated carrier, thereby to obtain the Fischer-Tropsch catalyst.

* * * * *